United States Patent [19]
Fukuyo

[11] Patent Number: 5,108,289
[45] Date of Patent: Apr. 28, 1992

[54] DENTAL ENDOSSEOUS IMPLANT

[76] Inventor: Sekio Fukuyo, 41-6, Shinsakae 1-chome, Naka-ku, Nagoya-shi, Aichi-ken, Japan

[21] Appl. No.: 683,038

[22] Filed: Apr. 10, 1991

[51] Int. Cl.$^5$ ............................................. A61C 8/00
[52] U.S. Cl. .................................................. 433/173
[58] Field of Search ............ 433/173, 174, 176, 201.1, 433/220

[56] References Cited

U.S. PATENT DOCUMENTS

| | | | |
|---|---|---|---|
| 4,468,201 | 8/1984 | Fukuyo | 433/176 |
| 4,934,935 | 6/1990 | Edwards | 433/174 |

*Primary Examiner*—John J. Wilson

[57] ABSTRACT

A dental endosseous implant having a generally cylindrical shape, which includes a leg portion embedded in an alveolar bone to form an artificial tooth root, and a head portion extending from one end of the leg portion to form a support upon which an artificial tooth is mounted. The implant is at least partially made of a metallic material having a thermal shape memory effect of deformation, which causes the leg portion to be bent with respect to the head portion in response to a variation of temperature of the implant after insertion of the leg portion into the alveolar bone.

13 Claims, 1 Drawing Sheet

5,108,289

DENTAL ENDOSSEOUS IMPLANT

BACKGROUND OF THE INVENTION

1. Field of the Invention

The present invention relates generally to a dental endosseous implant for oral implantology, and more particularly to a generally cylindrical or rod-like implant at least partially made of a thermal shape memory metallic material.

2. Discussion of the Prior Art

Various types of dental endosseous implants having various structures are known in the field of the oral implantology. Of the known types, a cylindrical or rod-like implant which extends straight over its entire length has been widely used in the art. FIG. 1 shows an example of this type of endosseous implant inserted or implanted in the alveolar bone of the lower jaw. That is, a cylindrical endosseous implant 2 is implanted in a cylindrical bore formed by a drill, for example, in a portion of the alveolar bone 4 on which an artificial tooth or denture is to be mounted. The cylindrical endosseous implant 2 is inserted a suitable depth into the cylindrical bore in the alveolar bone 4. The cylindrical implant 2 thus inserted in the alveolar bone 4 has a leg portion embedded in the bone 4 to serve as an artificial tooth root or fang, and a head portion extending up from the leg portion into the oral cavity to serve as a support upon which the artificial tooth is mounted.

However, the cylindrical implant 2 as described above tends to be removed or disengaged from the alveolar bone 4 during use, since the straight implant 2 is merely inserted in the bore in the alveolar bone 4. To avoid this drawback, it is proposed that a suitable thread is cut on the portion of the implant 2 which is embedded in the alveolar bone 4, so that the threaded portion of the implant 2 is securely held in engagement with the wall of the bore formed in the alveolar bone 4. In this case, however, the implant 2 may be rotated in the bone 4, and is therefore incapable of fixedly supporting the artificial tooth mounted thereon.

SUMMARY OF THE INVENTION

The present invention was developed in view of the prior art situations as described above. It is therefore an object of the invention to provide a cylindrical endosseous implant which is at least partially made of a thermal shape memory metallic material, and which is less likely to be removed from the alveolar bone, and free from a loose fit in the alveolar bone.

The above object may be attained according to the principle of the present invention, which provides a dental endosseous implant having a generally cylindrical shape, comprising a leg portion embedded in an alveolar bone to form an artificial tooth root, and a head portion extending from one end of the leg portion to form a support upon which an artificial tooth is mounted, the implant being at least partially made of a metallic material having a thermal shape memory effect of deformation, which causes the leg portion to be bent with respect to the head portion in response to a variation of temperature of the implant after insertion of the leg portion into the alveolar bone.

The endosseous implant provided according to the invention assumes a generally cylindrical shape, and is at least partially fabricated of a thermal shape memory metallic material which changes in configuration, due to a difference in temperature thereof before and after the implantation. Accordingly, the present implant is easily inserted into a bore formed in a alveolar bone while it has a straight cylindrical shape, and thereafter, the leg portion is inclined or bent a given angle relative to the head portion due to a rise in the temperature of the implant by means of heat transfer from the alveolar bone or positive heat application to the implant, for example. The implant is therefore firmly fixed in the alveolar bone soon after the insertion of the implant into the bone. In this case, the bonding strength between the alveolar bone and the leg portion of the implant is subsequently increased owing to regeneration of the alveolar bone occurring around the implant. Accordingly, the endosseous implant is unlikely to be easily removed from the alveolar bone or rotated in the bone, and is capable of supporting an artificial tooth mounted on the head portion extending outwardly from the alveolar bone, without suffering from displacement or jolting in the bone when the artificial tooth occludes with another tooth.

An entirety of the present implant may be made of the metallic material having a thermal shape memory effect of deformation.

In one form of the invention, at least one recess is formed in a longitudinally intermediate part of an outer surface of the leg portion, such that each recess extends in a direction parallel to a center line of the leg portion. In this case, the bonding strength between the endosseous implant and the alveolar bone is still further increased due to the regeneration of the alveolar bone, enabling the endosseous implant to more effectively function as an artificial tooth root upon which the artificial tooth or denture is mounted.

BRIEF DESCRIPTION OF THE DRAWINGS

The above and other objects, features and advantages of the present invention will become more apparent by reading the following description of the preferred embodiment when considered in connection with the accompanying drawings, in which.

DETAILED DESCRIPTION OF THE PREFERRED EMBODIMENT

Figure 1:
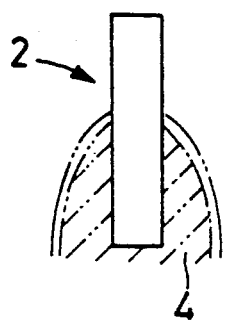
FIG. 1 is a schematic explanatory view showing a conventional dental endosseous implant inserted in the alveolar bone.
Figure 2:
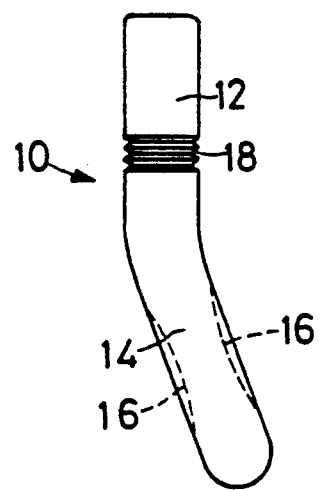
FIG. 2 is a front elevational view of one embodiment of a dental endosseous implant of the invention which has reverted to its original shape through a shape memory effect of deformation thereof appearing upon heat application thereto.

Referring first to FIG. 2, there is shown one embodiment of the present invention in the form of a cylindrical endosseous implant 10 which is bent at its longitudinally intermediate portion due to a shape memory effect of deformation of a metallic material. The cylindrical implant 10 consists of a head portion 12 and a leg portion 14 having a predetermined ratio of lengths. For example, the length of the head portion 12 ranges from 7 mm to 13 mm, preferably, from 9 mm to 11 mm, while the length of the leg portion 14 ranges from 9 mm to 17 mm, preferably, from 11 mm to 15 mm. The leg portion 14 is entirely embedded in the alveolar bone 4 to serve as an artificial tooth root or fang, while the head portion 12 formed integrally with the leg portion 14 is partially embedded in the alveolar bone 4 and extends up from one end of the leg portion 14, outwardly from the alveolar bone 4, so as to serve as a support upon which an artificial tooth structure is mounted. The head portion 12 includes a threaded section 18 formed at a lower part thereof adjacent to the above-indicated one end of the leg portion 14, such that the threaded section 18 is positioned in the alveolar bone 4. With this threaded section 18 engaging with the corresponding portion of the bone 4, the endosseous implant 10 is effectively prevented from coming off or being removed from the alveolar bone 4. It is to be noted that such a threaded or engaging section as described above may be provided or formed as needed. The present endosseous implant does not necessarily require the threaded section to practice the principle of the present invention.

The instant cylindrical endosseous implant 10 is bent at its longitudinally intermediate portion due to the shape memory effect of deformation in response to a change of the temperature thereof after the leg portion 14 is inserted in the alveolar bone 4, such that the leg portion 14 is inclined or bent a relatively small angle with respect to the head portion 12. That is, the endosseous implant 10 is made of a thermal shape memory metallic material which transforms upon variation in its temperature. For example, the implant 10 is entirely made of an alloy such as Cu-Zn-Al or Ti-Ni which has such a thermal shape memory effect of deformation. Since the endosseous implant 10 has a bent or curved shape as indicated in FIG. 2 as its original determinate shape, the implant 10 which has been deformed into a straight cylindrical shape at a lower temperature reverts to the original determinate shape upon heating thereof to a predetermined higher temperature, so that the leg portion 14 is inclined in a given direction by a given angle with respect to the head portion 12. Preferably, the angle formed by the inclined leg portion 14 and an extension line of the center line of the head portion 12 is suitably selected within a range of 15°-30°.

Figure 3:
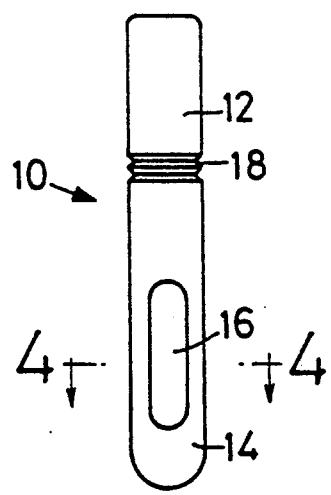
FIG. 3 is a side elevational view of the implant of FIG. 2, as viewed from the right-hand side of FIG. 2.
Figure 4:
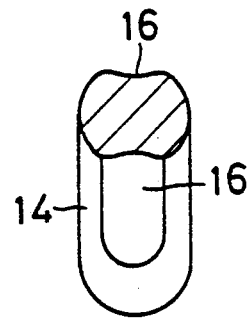
FIG. 4 is a fragmentary perspective view showing a cross sectional shape taken along line 4—4 of FIG. 3.
Figure 5:
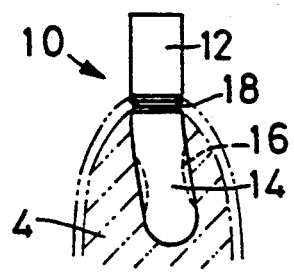
FIG. 5 is a schematic explanatory view showing the present endosseous implant of FIG. 2, which is inserted in the alveolar bone.

As is apparent from FIGS. 3 and 4, the leg portion 14 of the instant endosseous implant 10 has a pair of parallel recesses 16 formed in its outer surface at diametrically opposite portions thereof. These recesses 16 are formed in longitudinally intermediate parts of the leg portion 14 so as to extend over a given length in the longitudinal direction, and so as not to reach the longitudinally opposite end parts of the leg portion 14. The recesses 16 are formed in the diametrically opposite portions of the leg portion 14 which are opposite to each other in a direction in which the leg portion 14 is bent with respect to the head portion 12, such that the recesses 16 are open on the outer surface of the leg portion 14 in the direction of inclination of the leg portion 14, as shown in FIGS. 2 and 5.

There will be hereinafter described a procedure of inserting the thus constructed endosseous implant 10 into the alveolar bone 4. First, a cylindrical bore is formed by a drill, for example, in a portion of the alveolar bone on which an artificial tooth or denture is to be mounted. Then, the leg portion 14 of the uprightly extending or straight endosseous implant 10 is inserted or positioned in the cylindrical bore of the alveolar bone. Thereafter, the endosseous implant 10 inserted in the alveolar bone is heated to a given temperature by a suitable heating method, so that the implant 10 which has been deformed into the above-indicated straight shape reverts to its original determinate shape in which the leg portion 14 is inclined a given angle relative to the head portion 12. In this embodiment, a hole having a small diameter is formed in a portion of the implant 10 on one of diametrically opposite sides thereof on which the angle formed by the head and leg portions 12, 14 is larger than that on the other side, such that the hole extends into the free end portion of the leg portion 14. Namely, the hole is formed on the left-hand side of the implant 10 as seen in FIG. 2. The leg portion 14 of the implant 10 is heated by injecting a sterile physiological salt solution having a temperature around 45° C., for example, through the small hole formed in the implant 10 as described above. Upon heating of the leg portion 14, the endosseous implant 10 resumes its original determinate shape as shown in FIG. 2, with the leg portion 14 being inclined by a given angle inwards of the oral cavity, due to the thermal shape memory effect of the metallic material used for the implant 10. Consequently, the leg portion 14 is suitably forced against the wall of the bore in the alveolar bone 4, so that the implant 10 is firmly fixed in position with the leg portion 14 embedded in the alveolar bone 4. FIG. 5 illustrates the present endosseous implant 10 whose shape has been changed after the insertion into the alveolar bone 4.

It is desirable that the leg portion 14 of the implant 10 is heated so that the implant 10 is slowly bent with the lapse of time, to eventually assume the original memory shape, instead of being abruptly bent or deformed to the original memory shape at a time.

It is noted that the normal temperature of the implant 10 within the oral cavity of a living body is high enough to maintain the memory shape of the implant 10 even after the removal of the positively applied heat.

With the leg portion 14 embedded in the alveolar bone 4 as described above, biological regeneration of the bone 4 takes place according to the memory shape of the leg portion 14, assuring sufficiently firm bonding or anchoring between the alveolar bone 4 and the leg portion 14. In this condition, the instant endosseous implant 10 is capable of supporting an artificial tooth mounted on the head portion 12 formed integrally with the leg portion 14, without suffering from easy removal from the alveolar bone, or a loose fit in the same bone.

In the instant embodiment, the endosseous implant 10 is constructed such that the leg portion 14 is inclined a suitable angle with respect to the head portion 12, and such that the leg portion 14 has the recesses 16 formed in its outer surface. Thus, the present endosseous implant 10 is designed to be substantially similar to the natural tooth root, and therefore has an effectively improved function of supporting the artificial tooth when it occludes with another tooth. Further, since the recesses 16 are formed only in the longitudinally intermediate portions of the leg portion 14, the opposite end parts of the leg portion 14 located at the bottom and inlet of the bore of the alveolar bone 4 have a circular cross sectional shape, whereby the instant implant 10 is prevented from displacement or jolting in the bore of the alveolar bone 4 which results from a loose fit of the implant 10 in the bore.

When the cylindrical endosseous implant 10 is made of a shape memory metallic material, the implant 10 can be easily deformed into a desired inclined shape upon heat application thereto, after the insertion of the implant 10 having a straight cylindrical shape, since the material memorizes the desired shape, i.e., a suitably bent or inclined configuration. The instant implant 10 thus deformed by heat application is effectively secured or retained in the bore formed in the alveolar bone 4. Further, the formation of the longitudinally extending recesses 16 in the outer surface of the leg portion 14 allows for regeneration of the alveolar bone 4 and resultant integration of the leg portion 14 with the bone 4, assuring considerably firm bonding therebetween, without undesirable displacement of the implant 10, which would not be obtained with a cylindrical implant having no recesses.

While the present invention has been described in the presently preferred embodiment with a certain degree of particularity, it is to be understood that the invention is not limited to the details of the illustrated embodiment, but may be embodied with various changes, modifications and improvements which may occur to those skilled in the art, without departing from the spirit and scope of the appended claims.

Although the entire portion of the illustrated implant 10 is made of a metallic material having a thermal shape memory effect of deformation, the implant may be partially made of a thermal shape memory metal, provided that the desired memory shape can be resumed by heat application.

For instance, the endosseous implant 10 may have the leg portion 14 made of a thermal shape memory metal, and the head portion 12 made of a material, such as bioglass, which does not have a thermal shape memory effect of deformation.

While the pair of recesses 16 are formed in the diametrically opposite portions of the leg portion 14 of the implant 10 in the illustrated embodiment, the implant of the present invention may be provided with only one recess or no recess formed in its leg portion.

While the head portion 12 which extends from one end of the leg portion 14 to form a support for an artificial tooth structure assumes a cylindrical shape with a constant diameter, the shape of the head portion of the present implant is not limited to that of the illustrated embodiment. For example, a relatively upper part of the head portion may be provided with a threaded section or sections formed in the outer surface thereof, in addition to or in place of the threaded section 18, for the purpose of assuring secure attachement of an artificial tooth to the head portion 12. Further, the head portion (12) and the leg portion (14) of the present implant may be first formed independently of each other, and then bonded or fixed together by suitable bonding or fixing means after the insertion of the leg portion into the alveolar bone.

Further, the surface of the implant of the present invention may be finished, coated, or otherwise treated in an attempt to improve its compatibility with the alveolar bone, and facilitate the attachment of the artificial tooth to the implant.

For instance, the leg portion of the implant may be partially or totally coated with a bioceramic, bioactive or bioinert material. The thickness of the coating should be determined so that the coating does not affect the thermal shape memory effect of the material of the leg portion.

Alternatively, the surface of the leg portion may be finished by shot peening or shot blasting, so that the entire surface area of the leg portion may be considerably increased, thereby accelerating regeneration of the alveolar bone after the implantation of the present implant. The shot peening process provides an additional advantage. That is, the leg portion exhibits an increased mechanical strength (e.g., fatigue strength) after the implantation, due to a surface compressive residual stress applied thereto during the shot peening process.

What is claimed is:

1. A dental endosseous implant having a generally cylindrical shape, comprising a leg portion to be embedded in an alveolar bone to form an artificial tooth root, and a head portion extending from one end of said leg portion to form a support upon which an artificial tooth is mounted, said implant being at least partially made of a metallic material having a thermal shape memory effect of deformation, which causes said leg portion to be bent with respect to said head portion in response to a variation of temperature of the implant after insertion of said leg portion into said alveolar bone, said leg portion having at least one recess formed in a longitudinally intermediate part of an outer surface thereof, one of said at least one recess being open on one of diametrically opposite portions of said outer surface of said leg portion, in a direction in which said leg portion is bent with respect to said head portion.

2. A dental endosseous implant according to claim 1, wherein an entirety of said implant is made of said metallic material having a thermal shape memory effect of deformation.

3. A dental endosseous implant according to claim 1, wherein each of said at least one recess extends in a direction parallel to a center line of the leg portion.

4. A dental endosseous implant according to claim 3, wherein said at least one recess consists of a pair of recesses which are formed in said diametrically opposite portions of said outer surface of said leg portion.

5. A dental endosseous implant according to claim 1, wherein said head portion has a threaded section disposed adjacent to said leg portion, said threaded section engaging the alveolar bone to prevent the implant from being removed from the alveolar bone.

6. A dental endosseous implant according to claim 1, wherein said metallic material having a thermal shape memory effect consists of an alloy selected from a group consisting of Cu-Zn-Al and Ti-Ni alloys.

7. A dental endosseous implant according to claim 1, wherein said metallic material having a thermal shape memory effect of deformation causes said leg portion to be inclined with respect to said head portion by an angle within a range of 15° to 30°, when the temperature of said implant is changed after said leg portion is inserted into said alveolar bone.

8. A dental endosseous implant according to claim 1, wherein said head portion has a length of 7 mm-13 mm.

9. A dental endosseous implant according to claim 8, wherein said head portion has a length of 9 mm-11 mm.

10. A dental endosseous implant according to claim 1, wherein said leg portion has a length of 9 mm-17 mm.

11. A dental endosseous implant according to claim 10, wherein said leg portion has a length of 11 mm-15 mm.

12. A dental endosseous implant according to claim 1, wherein said leg portion is made of said metallic material having a thermal shape memory effect of deformation, and said head portion is made of a material other than said metallic material.

13. A dental endosseous implant according to claim 1, wherein said leg portion has a surface which is finished by shot peening.

* * * * *